United States Patent [19]

Wan

[11] Patent Number: 5,472,581
[45] Date of Patent: Dec. 5, 1995

[54] MICROWAVE PRODUCTION OF $C_2$ HYDROCARBONS, USING A CARBON CATALYST

[75] Inventor: Jeffrey K. S. Wan, Kingston, Canada

[73] Assignee: Queen's University, Kingston, Canada

[21] Appl. No.: 339,219

[22] Filed: Nov. 8, 1994

Related U.S. Application Data

[63] Continuation of Ser. No. 75,243, Jun. 11, 1993, abandoned.

[51] Int. Cl.[6] ................................................ C07C 2/00
[52] U.S. Cl. .................. 204/157.6; 204/157.43; 204/157.47; 204/168; 204/170; 204/171; 585/648
[58] Field of Search ............... 204/157.43, 157.47, 204/157.6, 168, 170, 171; 585/648

[56] References Cited

U.S. PATENT DOCUMENTS

| | | | |
|---|---|---|---|
| 4,574,038 | 3/1986 | Wan | 204/162 R |
| 4,975,164 | 12/1990 | Ravella et al. | 204/157.43 |
| 5,181,998 | 1/1993 | Murphy et al. | 204/157.6 |
| 5,198,084 | 3/1993 | Cha et al. | 204/157.47 |
| 5,205,912 | 4/1993 | Murphy | 204/157.43 |
| 5,266,175 | 11/1993 | Murphy | 204/157.43 |
| 5,277,773 | 1/1994 | Murphy | 204/170 |

FOREIGN PATENT DOCUMENTS 9202448  2/1992  WIPO ................. 204/157.43

*Primary Examiner*—John Niebling
*Assistant Examiner*—C. Delacroix-Muirheid
*Attorney, Agent, or Firm*—Richard J. Hicks

[57] ABSTRACT

$C_1$ and $C_2$ hydrocarbons may be produced under the action of pulsed microwave energy in a reactor containing activated charcoal as a catalyst/reactant. Methane and/or water is the other active ingredient and the product is primarily acetylene.

12 Claims, 3 Drawing Sheets

MICROWAVE PRODUCTION OF $C_2$ HYDROCARBONS, USING A CARBON CATALYST

This application is a continuation of application Ser. No. 08/075,243, filed Jun. 11, 1993, abandoned.

FIELD OF INVENTION

This invention relates to the production of $C_2$ hydrocarbons from water or methane. More particularly this invention relates to a microwave induced process for conversion of water or methane to $C_2$ hydrocarbons, using a carbon catalyst.

BACKGROUND OF INVENTION AND PRIOR ART

The $C_2$ hydrocarbons such as acetylene and ethylene are important primary feedstocks in the petrochemical industry and are frequently produced by cracking higher hydrocarbons.

Methane, thermodynamically the most stable hydrocarbon, is the most abundant component of natural gas, usually comprising over 90 mole percent of the hydrocarbon fraction of the gas. Methane is, of course, an important hydrocarbon fuel but it is highly desirable that it be available as a feedstock for manufacture of higher hydrocarbons such as acetylene and ethylene.

Traditionally acetylene has been prepared in a two step process from calcium oxide and carbon, which firstly produces calcium carbide.

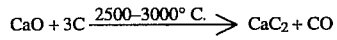

and then hydrolysis of the calcium carbide to produce acetylene $$CaC_2 + 2H_2O \rightarrow C_2H_2 + Ca(OH)_2$$

This process is, however, highly endothermic as is the high temperature decomposition of methane, with or without a limited quantity of oxygen.

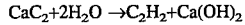

In U.S. Pat. No. 4,574,038, dated 4 Mar. 1986, to Wan, a process to convert methane to ethylene using microwave energy is described. In this process the methane is contacted with a powdered metal catalyst and subjected to a pulse train of microwave radiation.

Microwave energy is also employed in the process described in U.S. Pat. No. 4,975,164, dated 4 Dec. 1990 to Rayella et al, who converted $C_2$+hydrocarbons (i.e. $C_2$–$C_4$ saturated hydrocarbons) to primarily unsaturated hydrocarbons and hydrogen, in the presence of one or more plasma initiators. The plasma initiator may be metallic or non-metallic and may include a carbon initiator. It will be noted however, that the carbon initiator is not a reactant as there is already a surfeit of carbon for the reaction. In contrast when water or methane is converted to a $C_2$ or higher hydrocarbon there is a net deficiency of carbon which must be made up from another source of carbon, such as activated charcoal which is both a catalyst and a co-reactant.

Object of Invention

It is, therefore, an object of the present invention to provide a microwave induced process for conversion of methane into $C_2$+hydrocarbons using a powdered carbon catalyst which can act as a co-reactant in the reaction. Use of carbon as both a microwave catalyst and a co-reactant is very energy cost effective since the net endothermicity in this reaction is about 50% lower than that observed in direct methane conversion, without a co-reactant.

Another object of the invention is to provide a process to produce $C_1$ and $C_2$ hydrocarbons and especially acetylene using a carbon catalyst/co-reactant and reacting it with water, in the presence of pulsed microwaves.

Brief Statement of Invention

By one aspect of this invention there is provided a process for converting methane to $C_2$ hydrocarbons comprising:
providing methane in a reaction zone containing a carbon catalyst which is capable of absorbing microwave radiations; irradiating the methane, in the presence of said catalyst, with pulsed microwave radiation for a sufficient period of time to convert said methane to $C_2$ hydrocarbon products; and recovering said products.

By another aspect of this invention there is provided a process for producing $C_1$ and $C_2$ hydrocarbons comprising:
providing water in a reaction zone containing a carbon catalyst which is capable of absorbing microwave radiation; irradiating the water in the presence of said catalyst with pulsed microwave radiation for a sufficient period of time, to react said water with said carbon to thereby produce $C_1$ and $C_2$ hydrocarbon products; and
recovering said products.

DETAILED DESCRIPTION OF PREFERRED EMBODIMENTS

Figure 1:
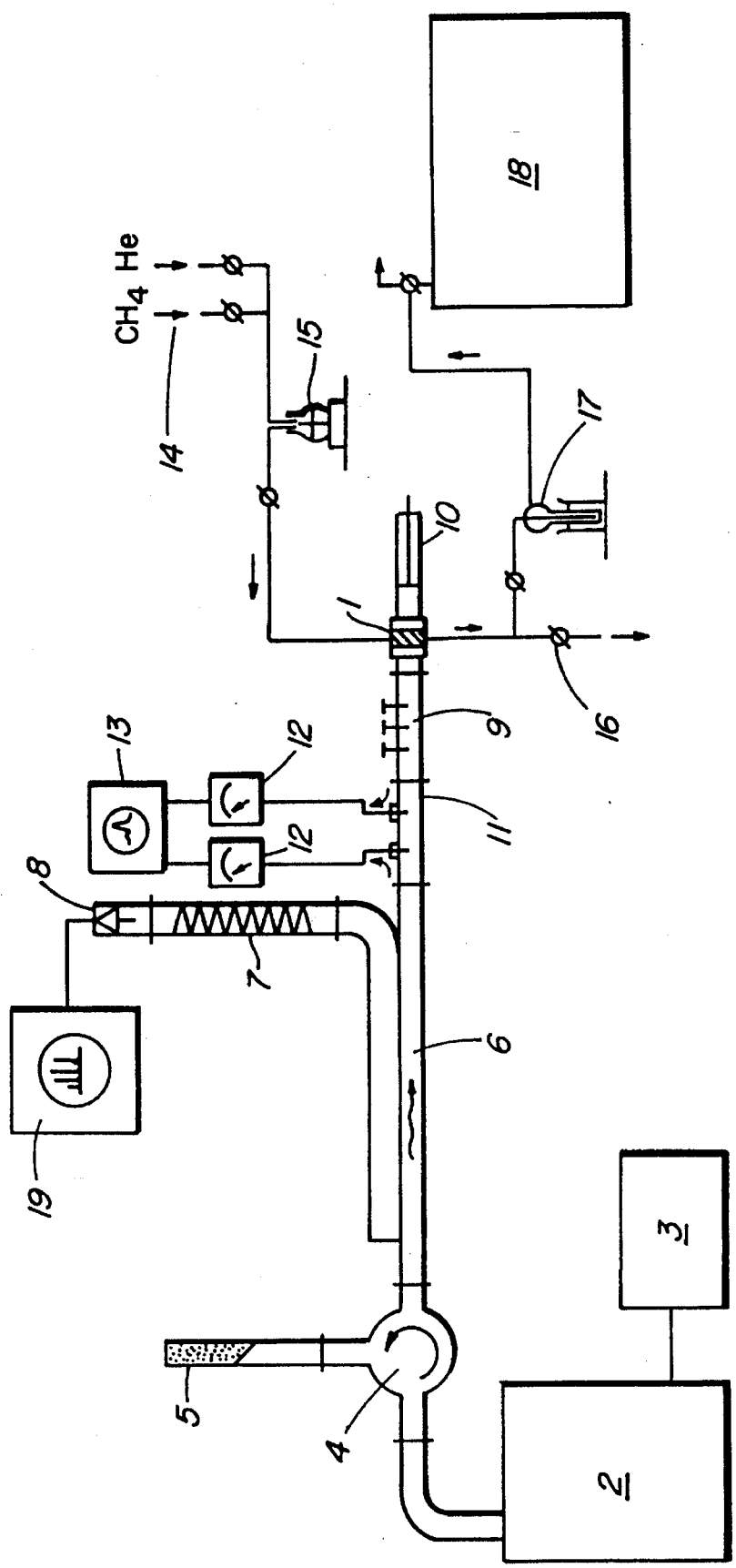
FIG. 1 is a schematic diagram of one embodiment of an apparatus for use in the present invention.

With reference to FIG. 1, there is shown a microwave waveguide reactor system 1, having a Cober variable 3 kW, 2.45 GHz magnetron, Model S3F/4091 power source 2. A custom built pulse controller 3 may be used to control the period, duty cycle and power level. A circulator 4 with a water cooled terminator 5 acts as an isolator to protect the microwave generator from reflected microwaves. A 20-db directional coupler 6 in combination with a 30-db attenuator 7, a crystal detector 8 and an oscilloscope 19 (Nicolet Explorer IIIA digital, model 204, for example) is used to monitor incident power amplitude and pulse width. Tuning is affected by a three-stub tuner 9 and a tunable short 10. Measurements of incident and reflected microwave power are effected with a cross guide coupler 11, power meters 12 and a digital oscilloscope 13 (e.g. Hitachi model VC-6023).

Microwaves from the magnetron 2 are transmitted to the reactor, essentially a 4 cm section of a 7.2×3.4 cm rectangular S-band waveguide with a pair of mica windows, which are transparent to the microwave radiation, making an air tight seal. The carbon catalyst (usually activated charcoal powder or pellets) is usually packed into a Pyrex® or quartz tube 7 cm long and 2 cm diameter (I.D.), and placed in the reaction cavity 1 so that its long axis is perpendicular to both the direction of propagation of the microwaves and the electric field so as to maximize exposure to the incident radiation. The reactants, $CH_4$ (14) and water (15) as selected, are introduced into cavity 1 via a drilled hole in the sidewall and the exit from the reactor is alternately connected to vacuum pump 16, or to cold trap 17 and gas chromatograph 18 (e.g. Hewlett-Packard 5890A) with thermal conductivity (T.C.D.) and flame ionization (F.I.D.) detectors connected in series.

EXAMPLE 1

5.4 g of activated carbon pellets (Norit RB 10.6) were packed into an approximately 20 cm³ quartz tube which was placed in the reaction cavity as described above and evacuated for 25 seconds. An atmosphere of helium was then introduced and the tube was subjected to 0.5 seconds of pulsed microwave irradiation, at 1.6–2.8 kW average power in packets of about 1 ms pulses, followed by a 25 second dark period. On line product analysis was carried out using a gas chromatograph sampling system as described above. Products were separated using a 6 ft×⅛" stainless steel column packed with Porapak®N. Identification of products was effected by comparing their respective retention times with those of appropriate standards. The result of this experiment is shown in Table 1 below, as the control, i.e. no water added.

The test was repeated with the addition of 2.5–3.1 g water (Water/carbon ratio 0.45/1), for varying irradiation times ranging from 5–30 seconds. The results are also tabulated in Table 1.

TABLE I

Products from the microwave induced reaction of water and carbon:
Microwave power: 1.87 kW; Pulse duration: 0.5 s; Water/Carbon: 0.45.

| | Concentration (counts) | | | |
|---|---|---|---|---|
| Irradiation time (s) | He/Carbon | He/Water/Carbon | | |
| Product | 30 | 5 | 15 | 30 |
| Methane | 2.68 | 8.44 | 19.87 | 35.78 |
| Ethane | — | — | 1.22 | 2.39 |
| Ethylene | — | — | 2.73 | 5.17 |
| Acetylene | 3.15 | 23.75 | 64.16 | 115.11 |
| Carbon dioxide* | 1.66 | 6.84 | 25.74 | 47.38 |
| Carbon Monoxide** | nd | nd | nd | nd |
| Oxygen** | nd | nd | nd | nd |

*Values for $CO_2$ may be low because it chemisorbs strongly on carbon than other reported products (42).
**Undetermined due to separation problems from the oxygen peak.

EXAMPLE 2

The 20 cm³ quartz tube of Example 1 was packed with 8 g of dried activated carbon pellets (Norit®RB 10.6) under a helium atmosphere. The tube was then placed in the reaction cavity and the system evacuated for 25 minutes. The system was then purged with helium several times to remove residual air and moisture. After equilibration for 30 minutes, the tube was subjected to 500 ms pulses of microwave irradiation at 1.6–2.8 kW average power followed by a 25 second rest period. The products were analyzed as in Example 1. In the blank experiment thus far described only minor amounts of acetylene were observed in the off gases, presumably as a result of residual water adsorbed on the carbon. The experiment was, however, repeated with introduction of methane at a pressure of 100 kpa and for different power levels. The resultant gases were analyzed and the results are tabulated in Table 2.

TABLE 2

Product yield and selectivity from the reaction of methane and carbon at various power levels:
Total irradiation time: 50 s; Pulse duration 0.5 s; Rest period: 25 s.

| | Yield (counts) | | Product Selectivity (%) | |
|---|---|---|---|---|
| Power (kw) Product | 2.48 | 2.8 | 2.48 | 2.8 |
| Ethane | 5.86 | 29.96 | 0.98 | 1.21 |
| Ethylene | 14.00 | 205.31 | 2.34 | 8.30 |
| Acetylene | 552.04 | 2195.70 | 92.40 | 88.77 |
| $C_3$ | 25.57 | 42.52 | 4.28 | 1.72 |

As can be seen, upon irradiation of carbon sorbed with methane a substantial amount of $C_2$ hydrocarbons were produced. Acetylene constituted between 80 and 95% of all the products. In high power and long time irradiation experiments, appreciable amounts of $C_3$ hydrocarbons were also observed.

Figure 2:
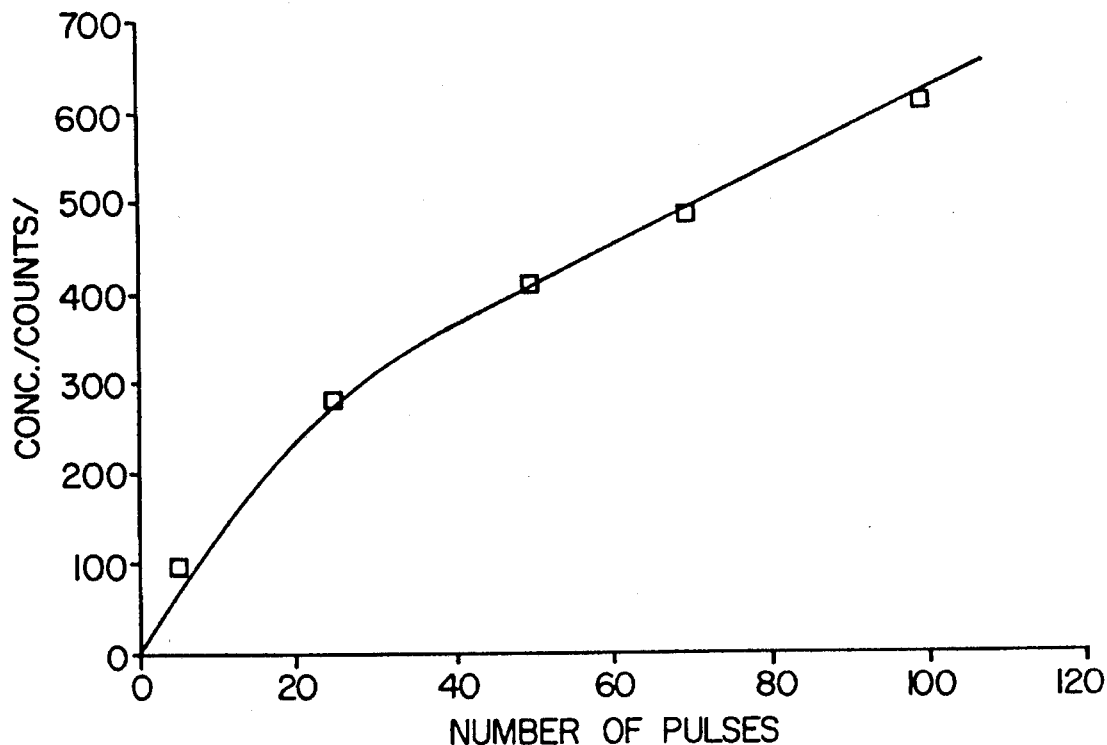
FIG. 2 is a graph illustrating yield of acetylene relative to microwave pulse energy.
Figure 3:
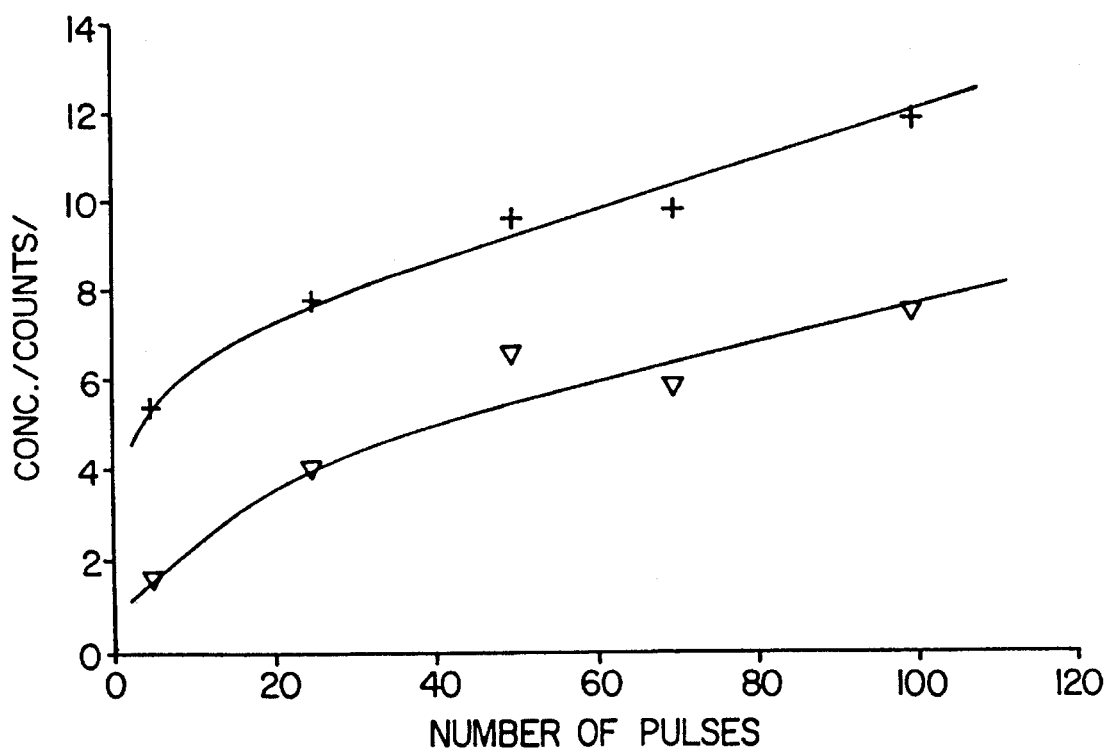
FIG. 3 is a graph illustrating the yield of ethylene (squares) and $H_2$ and ethane (diamonds) relative to microwave pulse energy.

The yields of acetylene, ethylene and ethane versus the number of pulses are shown in FIGS. 2 and 3. The evolution of acetylene increases with the number of pulses, whereas the yields of ethane and ethylene increased with the number of pulses but plateaued after about 20 pulses, i.e. 10 s of irradiation time. The observed gradual decline in the rate of acetylene production is attributable to increased desorption of methane as the surface temperature increases with time and to the increased probability for acetylene to undergo secondary reactions.

Figure 4:
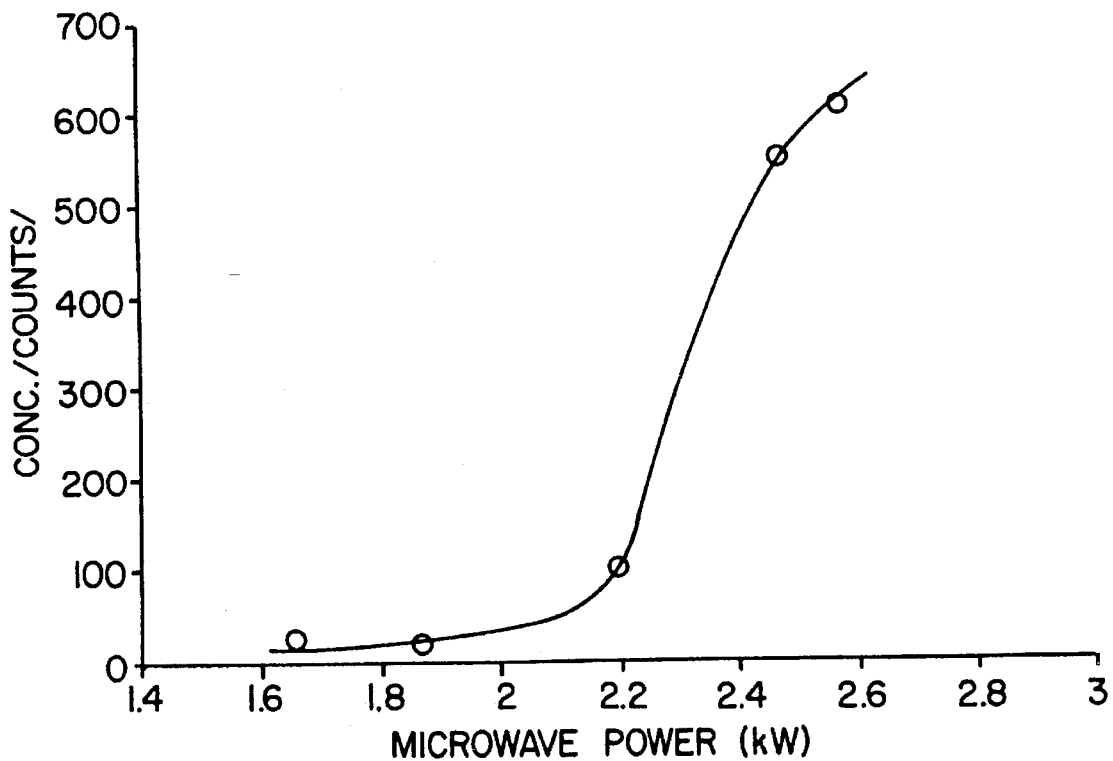
FIG. 4 is a graph illustrating effect of incident microwave power on acetylene production.

FIG. 4 shows the effect of peak power on the production of acetylene. An increase in incident microwave power accelerates the rate of reaction and illustrates that peak power is important to the efficiency of the reaction. The fact that relatively small yields were observed at low power levels indicates that, under the applied experimental conditions, the microwave energy supplied was not sufficient to raise the bed temperature to the minimum surface temperature required to initiate the reaction. A fast rise in the yield of acetylene is explained by the fact that high microwave power readily heats the carbon surface to the activation temperature. However, high power also gives rise to a high heating rate of the catalyst bed which may not cool down sufficiently between microwave pulses. This leads to high mobility of the adsorbed product species and a subsequent rise in probability for secondary reactions to occur.

EXAMPLE 3

Figure 5:
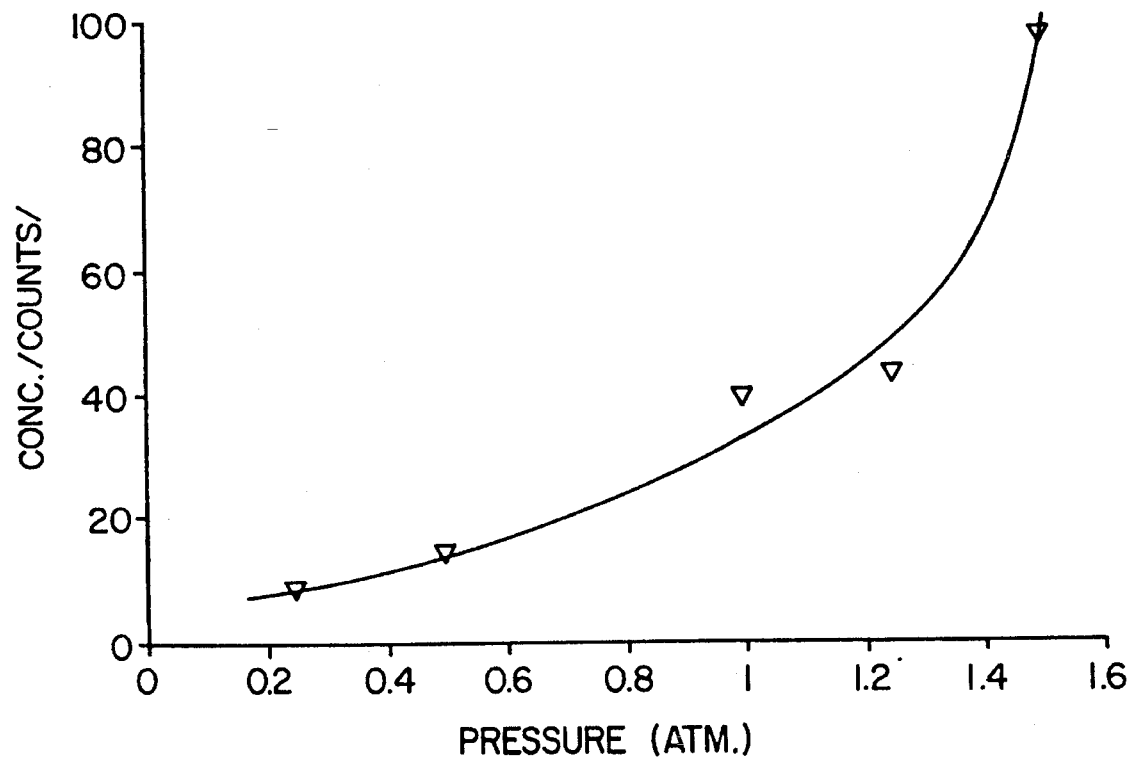
FIG. 5 is a graph illustrating the effect of methane pressure on acetylene production.

The procedure of example 2, was repeated with the introduction of methane at pressures varying between about 0–2 and 1.5 atmospheres. The resultant gases were analyzed and the results are shown in FIG. 5. It will be observed that as the initial methane pressure is increased the yield of acetylene increases almost exponentially.

I claim:

1. A process for converting methane to acetylene consisting of:

providing a reaction zone containing a carbon bed in a form which absorbs microwave radiations; introducing methane into said reaction zone;

irradiating said methane and said carbon bed with pulsed microwave radiations for a sufficient period of time to raise said bed to a surface temperature just sufficient to initiate a reaction to convert said methane to at least 80% acetylene and permit said bed to cool below said initiation temperature between microwave pulses; and recovering said acetylene.

2. A process as claimed in claim 1 wherein said carbon bed comprises activated carbon pellets.

3. A process as claimed in claim 2 wherein said microwave radiation wavelength is in the range of about 1.5–3.0 GHz.

4. A process as claimed in claim 3 wherein said microwave radiation is supplied in pulses of 500 ms to 10 seconds with off times of about 20 to 60 seconds.

5. A process as claimed in claim 4 wherein said microwave radiation has an incident power in the range 1.5–2.8 kW.

6. A process as claimed in claim 1 wherein said methane is provided at a pressure in the range 0.2 to 1.5 atmospheres.

7. A process for producing acetylene consisting of:

providing a reaction zone containing a carbon bed in a form which absorbs microwave radiations;

introducing water into said carbon bed;

irradiating said bed with pulsed microwave radiations for a sufficient period of time to raise said bed to a surface temperature just sufficient to initiate a reaction between said water and said carbon to thereby produce at least 80% acetylene and permit said bed to cool below said initiation temperature between microwave pulses; and recovering said acetylene.

8. A process as claimed in claim 7 wherein said carbon bed comprises activated carbon pellets.

9. A process as claimed in claim 8 wherein said microwave wavelength is in the range of about 1.5–3.0 GHz.

10. A process as claimed in claim 9 wherein said microwave radiation is supplied in pulses of 500 ms to 10 seconds with off times of about 20 to 60 seconds.

11. A process as claimed in claim 10 wherein said microwave radiation has an incident power in the range 1.6–2.8 kW.

12. A process as claimed in claim 11 wherein said power is in the range 1.87 to 2.8 kW.

* * * * *